United States Patent [19]

Kanegae et al.

[11] 4,181,005

[45] Jan. 1, 1980

[54] HYDROGEN DETECTOR

[75] Inventors: Naomichi Kanegae; Ichiro Ikemoto, both of Mito, Japan

[73] Assignee: Doryokuro Kakunenryo Kaihatsu Jigyodan, Tokyo, Japan

[21] Appl. No.: 856,804

[22] Filed: Dec. 1, 1977

[30] Foreign Application Priority Data

Dec. 6, 1976 [JP] Japan .................................. 51/146311
Dec. 7, 1976 [JP] Japan .................................. 51/146789

[51] Int. Cl.$^2$ ................................................ G01N 7/10
[52] U.S. Cl. ............................................ 73/19; 73/23
[58] Field of Search ................ 73/23, 19; 340/237 R, 340/421; 176/19 R, 38

[56] References Cited

U.S. PATENT DOCUMENTS

| 2,882,212 | 4/1959 | Beard | 73/23 X |
| 3,060,726 | 10/1962 | Weber | 73/19 |
| 3,426,579 | 2/1969 | Lebel et al. | 73/23 |
| 3,731,523 | 5/1973 | Vissers et al. | 73/19 |

FOREIGN PATENT DOCUMENTS 1442159 5/1966 France ......................................... 73/23

Primary Examiner—James J. Gill
Attorney, Agent, or Firm—Wenderoth, Lind & Ponack

[57] ABSTRACT

A hydrogen detector of the type in which the interior of the detector is partitioned by a metal membrane into a fluid section and a vacuum section. Two units of the metal membrane are provided and vacuum pipes are provided independently in connection to the respective units of the metal membrane. One of the vacuum pipes is connected to a vacuum gauge for static equilibrium operation while the other vacuum pipe is connected to an ion pump or a set of an ion pump and a vacuum gauge both designed for dynamic equilibrium operation.

6 Claims, 9 Drawing Figures

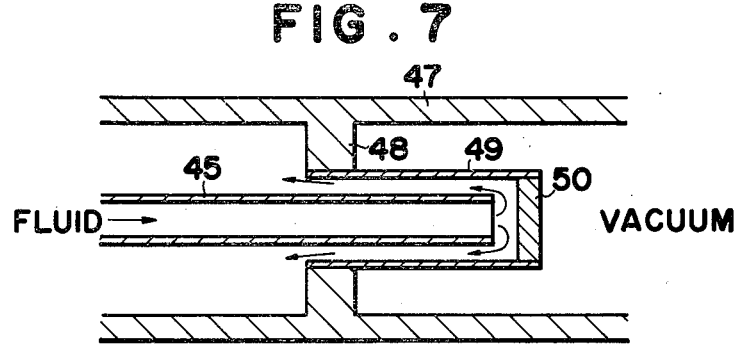
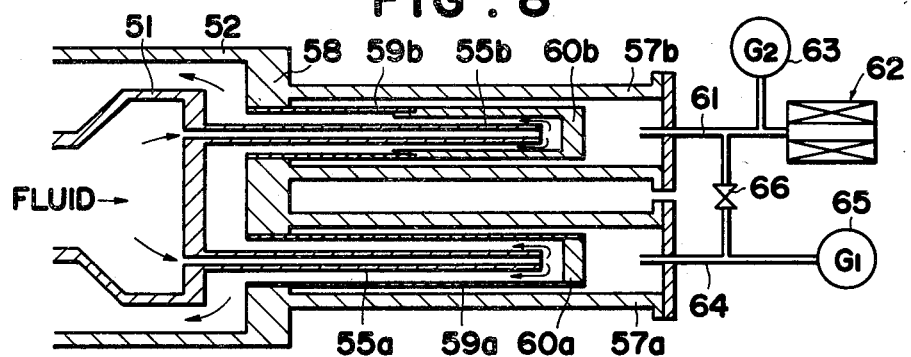
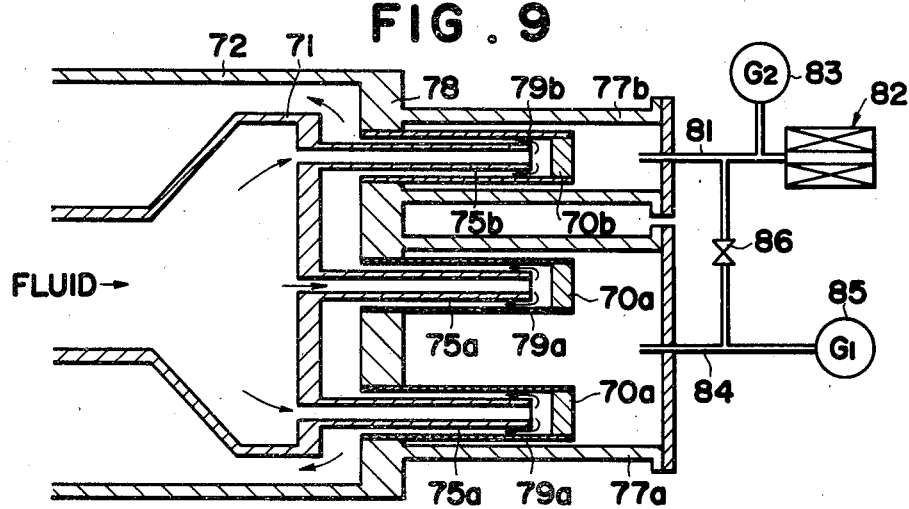

HYDROGEN DETECTOR

BACKGROUND OF THE INVENTION

This invention relates to an apparatus for detecting hydrogen contained in fluids such as liquid sodium, and various kinds of gas.

In a fast breeder, liquid sodium is used as a coolant and the heat accumulated in sodium is transferred into water in a vapor generator. In this case, if water leaks into sodium in the vapor generator, there takes place a vehement reaction between sodium and water to give rise to various sorts of trouble. As hydrogen is produced in this reaction, a hydrogen detector is usually provided in the sodium circulation loop having a vapor generator or in the cover gas in case the vapor generator is of the type having a cover gas space, in order to find out such water leaks as possible as early.

Generally, a conventional hydrogen detector, as illustrated in FIG. 1, has a construction in which the interior of the detector is partitioned by a metal membrane 3 into a fluid section 1 designed to allow passage therethrough of sodium or gas which may contain hydrogen, and a vacuum section 2 connected to an ion pump 6 by a pipe 4 provided with a stop valve 5. A vacuum gauge 7 for measuring low degrees of vacuum and another vacuum gauge 8 for measuring high degrees of vacuum are provided in connection to the vacuum pipe 4. Usually, nickel is used for the metal membrane 3. There are generally employed two types of operation for such hydrogen detector: static equilibrium operation and dynamic equilibrium operation, with the latter type of operation being used for ordinary measurements. In the static equilibrium operation, the stop valve 5 is kept closed and the partial pressure of hydrogen in the vacuum system is equalized with that in the fluid by the hydrogen which passes through the metal membrane 3, and the value of such partial pressure, that is, hydrogen concentration in the fluid, is measured by using chiefly the vacuum gauge 7 low degrees of vacuum. In the dynamic equilibrium operation, the stop valve 5 is opened and hydrogen concentration in the fluid is determined from the output value of the ion pump 6 in the operative state or from the value indicated by the vacuum gauge 8 for high degrees of vacuum. For determining hydrogen concentration in the fluid from the ion pump output value or from the reading of the vacuum gauge for high degrees of vacuum in the dynamic equilibrium operation, there is normally used a "calibration curve" obtained from a calibration test conducted before performing the normal measurement. This calibration curve is obtained in the following way: the hydrogen concentration in the fluid is changed stepwise, and the above-mentioned static equilibrium operation and dynamic equilibrium operation are carried out alternately while maintaining the condition free from variation of hydrogen concentration in each step to determine the interrelationship between the measurements by the two types of operation.

The essential conditions for high-precision hydrogen detector are that a calibration curve with a high accuracy can be obtained, that is, hydrogen concentration can be measured correctly in the static equilibrium operation during the calibration test, and that any change of hydrogen concentration in the fluid can be measured at a high accuracy during the ordinary dynamic equilibrium operation, and naturally the respective parts of the detector are required to have the configuration and size that come up to these conditions.

The optimum conditions for the static equilibrium measurement can be determined from the graph of FIG. 2. Assuming that the ratio $A/d$ (cm) of metal membrane surface area A ($cm^2$) to membrane thickness d (cm) and the amount of gas discharge $q^*$ (mmHg.l/sec) from the unit surface area of the internal wall surface in the vacuum section are constant, the smaller the internal wall surface area Ap ($cm^2$) in the vacuum section is, the higher becomes the measurement precision. For instance, in the case of a hydrogen detector using a metal membrane with surface area (A) of 200 $cm^2$ and thickness (d) of 0.05 cm, $A/d$ is $4 \times 10^3$ cm. Also, since the maximum possible amount of gas discharge $q^*$ from the internal wall surface in the vacuum system at high temperatures is around $10^{-11}$ mmHg.l/sec, the wall surface area Ap in the vacuum system must be smaller than 450 $cm^2$.

However, in the hydrogen detector of the conventional construction such as shown in FIG. 1, two vacuum gauges 7, 8, the stop valve 5 and the ion pump 6 must be connected to the vacuum pipe 4, and hence it is extremely difficult to regulate the internal wall surface area of the vacuum system within the optimum conditions.

SUMMARY OF THE INVENTION

The object of this invention is to provide a hydrogen detector which is free from the defects of the prior art and which allows a high-precision calibration test and hence is high in accuracy of measurement in the ordinary operations and also simple in operation procedure for the calibration test.

Briefly, this invention provides a hydrogen detector of the type in which the interior of the detector is partitioned by a metal membrane into a fluid section and a vacuum section. The detector according to this invention is characterized in that two units of the metal membrane are provided and vacuum pipes are provided independently in connection to the respective units of the metal membrane. One of the vacuum pipes is connected to a vacuum gauge for static equilibrium measurement while the other vacuum pipe is connected to an ion pump or a set of an ion pump and a vacuum gauge both designed for dynamic equilibrium measurement.

The metal membrane for static equilibrium measurement is preferably greater in surface area and smaller in thickness than the metal membrane for dynamic equilibrium measurement.

The metal membranes used in this invention are preferably tubular in shape, closed at the protuberant end, and extend into the respective vacuum pipes. A fluid inlet pipe communicating with the fluid section is inserted into each of the tubular metal membranes.

DESCRIPTION OF THE DRAWINGS

FIG. 7 is a schematic illustration of another embodiment of the tubular metal membrane portion; and FIGS. 8 and 9 are schematic illustrations of other embodiments of the hydrogen detector according to this invention.

DETAILED DESCRIPTION OF THE INVENTION

Figure 1:
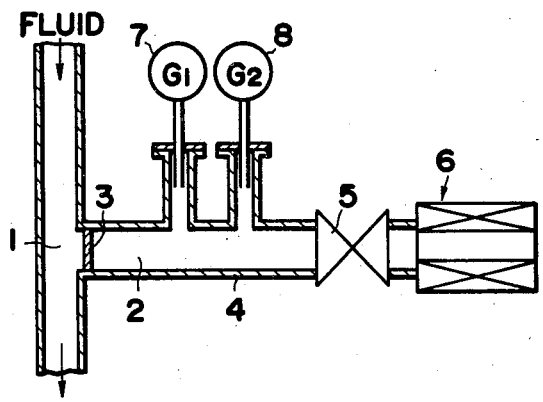
FIG. 1 is a schematic illustration of a prior art hydrogen detector.
Figure 3:
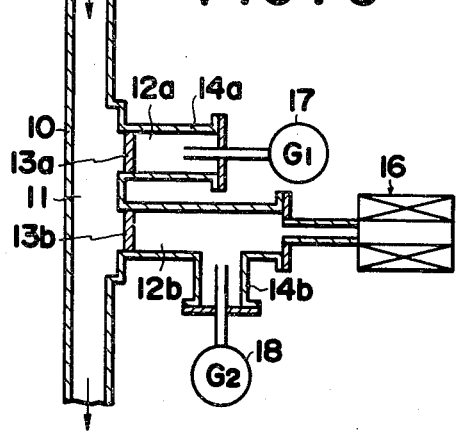
FIGS. 3, 4 and 5 are schematic illustrations of some embodiments of the hydrogen detector according to this invention.

Referring to FIG. 3, there is shown a schematic illustration of one embodiment of hydrogen detector according to this invention. It will be seen that two metal membranes 13a and 13b are provided to a fluid pipe 10 through which a fluid such as liquid sodium or gas passes, and vacuum pipes 14a and 14b are connected independently to the respective metal membranes 13a and 13b. Thus, the interior of the detector is partitioned by the metal membranes 13a and 13b into a fluid section 11 and two vacuum sections 12a and 12b. A vacuum gauge 17 for measurement of low degrees of vacuum is provided in connection to one of the vacuum pipes 14a to constitute a static equilibrium measuring system, while an ion pump 16 and a vacuum gauge 18 for measurement of high degrees of vacuum are provided in connection to the other vacuum pipe 14b to constitute a dynamic equilibrium measuring system. Although it is preferred to provide both metal membranes 13a and 13b adjacent to each other, they may be provided remote from each other. A pump for preliminarily and roughly exhausting gas in each of the vaccum sections 12a, 12b is necessary, but is not illustrated in FIG. 3, as well as the subsequent Figures, for simplification. Ordinary measurement of hydrogen concentration in the fluid can be accomplished in a conventional way. That is, the ion pump 16 is operated to let hydrogen in the fluid penetrate through the metal membrane 13b to enter the vacuum section 12b, and the output value of the ion pump 16 or the value indicated by the vacuum gauge 18 is measured and collated with the previously obtained calibration curve, hydrogen concentration in the fluid is varied stepwise and measurements by the static equlibrium measuring system and dynamic equlibrium measuring system are carried out simultaneously while maintaining a condition free of variation of hydrogen concentration in each step to determine the interrelationship between the measured values by both systems. If the static equilibrium measuring system and the dynamic equilibrium measuring system are separated from each other as in this invention, the internal wall surface area of the vacuum pipe 14a in the static equilibrium measuring system can be reduced to provide an improvement in measuring precision, and hence in calibration accuracy, in the static equilibrium operation, and also the operation of the valve (such as a numeral 5 in FIG. 1) for switching of the static and dynamic equilibrium operations during the calibration test is unnecessitated.

Figure 2:
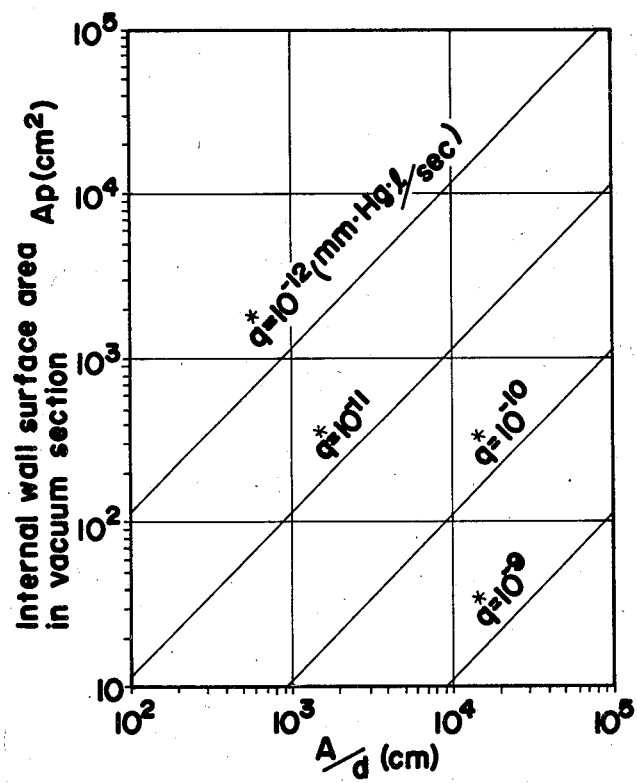
FIG. 2 is a graph illustrating the method for determining the optimum conditions for the static equilibrium measurement.
Figure 4:
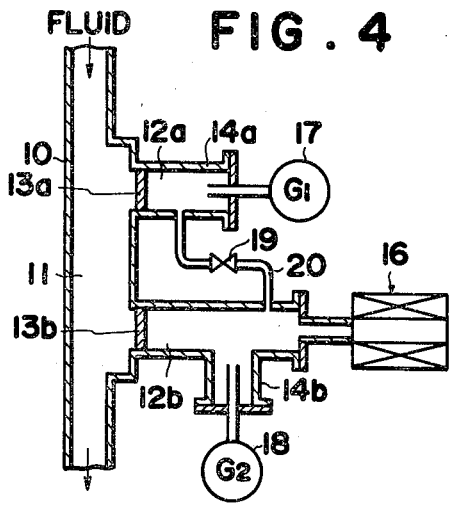

FIG. 4 shows another embodiment of hydrogen detector according to this invention. In this embodiment, the vacuum pipe 14a in the static equilibrium measuring system and the vacuum pipe 14b in the dynamic equilibrium measuring system is connected to each other by a pipe 20 provided with a stop valve 19. The stop valve 19 is kept closed during the calibration operation and the normal dynamic equilibrium operation, and hence the movements of the detector in these operations are same as in the embodiment of FIG. 3. As is apparent from the graph of FIG. 2, it is desirable to minimize the amount of gas discharge q* from the internal wall surface of the vacuum system in the static equilibrium measuring operation. Therefore, baking is sometimes required in the course of operation, and also such baking is indispensable when replacing the damaged vacuum gauge 17. In such a case, removal of hydrogen in the vacuum section 12a of the static equilibrium measuring system and baking can be accomplished by opening the stop valve 19. Of course, other pump may be provided for this baking. In case of employing a construction where both vacuum pipes 14a and 14b are connected to each other by the pipe 20 provided with such stop valve 19, it needs to arrange the two metal membranes 13a and 13b as close to each other as possible.

Figure 5:
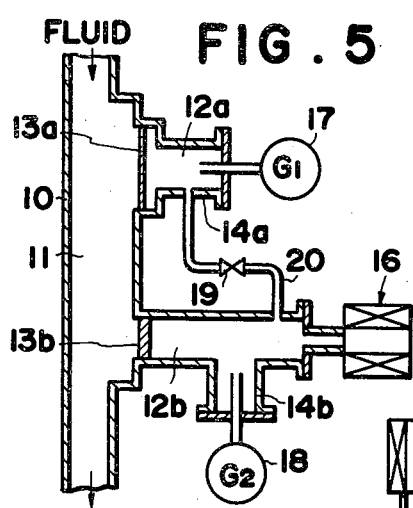

FIG. 5 shows still another embodiment of this invention. This embodiment is substantially same in construction, operation and use as the embodiment of FIG. 4, but in this embodiment, the metal membrane 13a of the static eqilibrium measuring system is greater in surface area A and smaller in thickness d than metal membrane 13b of the dynamic equilibrium measuring system. As noted from FIG. 2, a greater A/d ratio leads to an improvement in measuring accuracy for the calibration test.

Figure 6:
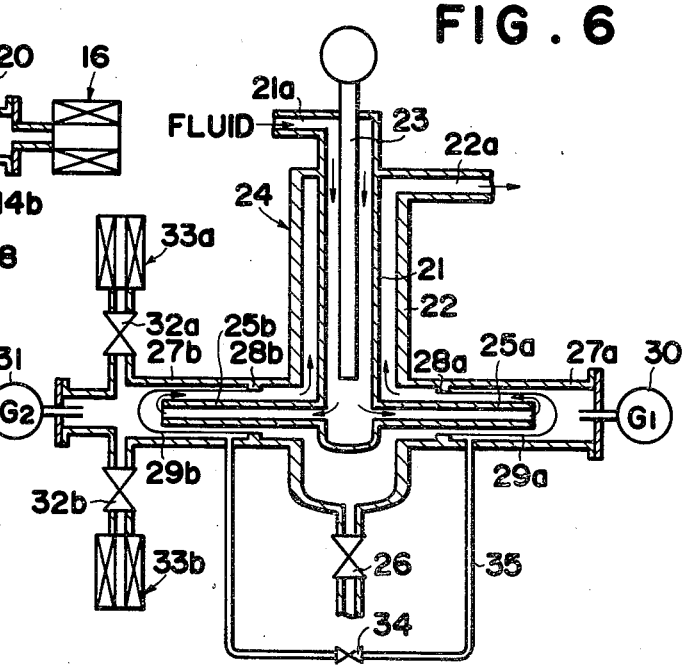
FIG. 6 is a diagrammatic structural drawing of still another embodiment of the hydrogen detector according to this invention.

FIG. 6 is a schematic structural diagram illustrating a further embodiment of hydrogen detector according to this invention. The fluid passage is adapted with a heater-incorporated economizer 24 comprising an inner pipe 21, an outer pipe 22 and a heater 23 inserted into the inner pipe 21. The bottomed inner pipe 21 is provided with two openings in its side wall close to its lower end, and the fluid inlet pipes 25a and 25b are connected to the respective openings. The outer pipe 22 is provided with a drain valve 26 at its lower end and has connected to its side wall two pipes 27a and 27b so arranged as to surround the fluid inlet pipes 25a and 25b, respectively. Each of the pipes 27a and 27b has provided on its interior a support block 28a (28b), and an end-closed cylindrical metal membrane 29a (29b) is secured to the block 28a (28b) so as to cover the fluid inlet pipe 25a (25b). Thus the interior of each of the pipes 27a, 27b is partitioned by the metal membrane 29a (29b) into a fluid section and a vacuum section. The pipe 27a has connected thereto a vacuum gauge 30 for measurement of static equilibrium pressure while the pipe 27b has connected thereto a vacuum gauge 31 for measurement of dynamic equilibrium pressure and two ion pumps 33a and 33b with different discharge rates through switch valves 32a and 32b, respectively. The both pipes 27a and 27b are also connected to each other by a pipe 35 provided with a stop valve 34.

The fluid to be measured enters from the top inlet end 21a of the inner pipe 21, flows down in the inner pipe 21, passes through the fluid inlet pipes 25a, 25b, turns back at the ends of said pipes 25a, 25b, rises up between the inner pipe 21 and outer pipe 22 and discharges out from the outlet 22a, as indicated by arrows in FIG. 6. In this course of fluid passage, hydrogen in the fluid diffuses through the metal membranes 29a, 29b. In the normal dynamic equilibrium operation, in case the hydrogen concentration in the fluid is low, the switch valve 32a is opened while the switch valve 32b is closed and the ion pump 33a with smaller discharge rate is operated to measure the hydrogen concentration, and in case the hydrogen concentration in the fluid is high, the switch valve 32a is closed while the switch valve 32b is opened and the ion pump 33b with greater discharge rate is operated to measure the hydrogen concentration. Use of the two ion pump with different discharge rates is advantageous in that a wider scope of measurement is allowed. By providing a cylindrical structure closed at its one end to the metal membrane, as illustrated in FIG. 6, it is easy to make such metal membranes with uniform thickness, and the membrane surface area can be increased while reducing the membrane thickness with no fear of sacrificing strength, resulting in improved precision of measurement. Also, since each tubular metal membrane is secured at one location, its joining work is easy. Further, any elongation of the tubular metal membrane by thermal expansion is absorbed by the free end of the tubular membrane, thus eliminating any risk of building up stress by temperature change. Moreover, since each fluid inlet pipe is disposed inside the associated tubular metal membrane, it is possible to let the fluid flow smoothly without stagnating in the tubular membrane.

Other structure of such tubular membrane may be employed in this invention. For instance, as shown in FIG. 7, a metal membrane 4a is cylindrical in shape, with both ends thereof opened, and the proximal end of the cylindrical metal membrane is secured to a support block 48 provided on the interior of an outer pipe 47. An end plate 50 made of the same material as the support block 48 is provided at the protuberant end of the cylinder to close it. Other arrangements including the route of fluid passage are same as in the embodiment of FIG. 6, so that it needn't to describe them here again. The numeral 45 is a fluid inlet pipe. If such cylindrical metal membrane is used, there is no need of curving the protuberant end and it is merely required to form the cylindrical portion alone, so that it becomes easier to uniformalize the membrane thickness. For instance, 0.5 mm±0.02 mm finish is made possible, allowing much improvement of detection accuracy.

FIGS. 8 and 9 show further embodiments of the hydrogen detector according to this invention. In the embodiment of FIG. 8, a block 58 having two circular openings is provided to an outer pipe 52, and vacuum side cylinders 57a, 57b are provided oppositely to the outer pipe 52 so as to cover the respective openings in the block 58. In one of the openings in the block 58 is provided a thick-walled short tubular metal membrane 59b extending into the vacuum side cylinder 57b, with the end of the tubular metal membrane 59b being joined to an end of a cylindrical tube 60b of which the protuberant end is closed. In another opning in the block 58 is provided a thin-walled elongated tubular metal membrane 59a extending into the vacuum side cylinder 57a, with the protuberant end of the tubular metal membrane 59a being closed by an end plate 60a. The distance from the block 58 to the end of the end tube 60b is equal to the distance from the block 58 to the end plate 60a. Inserted into the respective tubular metal membranes 59a and 59b are the fluid inlet pipes 55a, 55b of the same configuration, with the proximal ends of the respective fluid inlet tubes being connected to a common inner pipe 51. The tubular metal membrane 59b with large thickness and small surface area is used for dynamic equilibrium operation while the metal membrane 59a with small thickness and large surface area is used for static equlibrium operation. Employment of such end tube arrangement and similarly configured fluid inlet pipes makes it possible to equalize the fluid resistance in its passage.

In the embodiment of FIG. 9, a block 78 having three circular openings is provided internally to an outer pipe 72, and there are also provided oppositely to the outer pipe 72 a vacuum side cylinder 77b designed to cover only one opening in the block 78 and another vacuum side cylinder 77a adapted to cover the remaining two openings in the block. Provided in one of the openings in the block 78 is a thickwalled tubular metal membrane 79b extending into the vacuum side cylinder 77b, and provided in the remaining two openings in the block 78 are the thin-walled tubular metal membranes 79a, 79b extending into another vacuum side cylinder 77a, with the protuberant end of each of the tubular metal membranes 79a, 79b being closed by an end plate 70a, 70b. Inserted into the respective tubular metal membranes 79a and 79b are the fluid inlet pipes 75a, 75b which are connected to a common inner pipe 71. As two thin-walled tubular metal membranes 79a are provided in parallel relation to each other in the vacuum side cylinder 77a, there is provided in this cylinder 77a twice as large membrane surface area as in the cylinder 77b where only one thick-walled tubular metal membrane 79b is provided, and hence the former is used for the static equilibrium operation. Obviously, the membrane surface area can be increased corresponding to the number of thin-walled tubular metal membranes 79a provided.

In either of the embodiments of FIGS. 8 and 9, the vacuum side cylinder 57b, 77b containing the thick-walled tubular metal membrane 59b, 79b is connected to an ion pump 62, 82 and a vacuum gauge 63, 83 by a pipe 61, 81, while another vacuum side cylinder 57a 77a containing the thin-walled tubular metal membrane (s) 59a, 79a is connected to a vacuum gauge 65, 85 by a pipe 64, 84. The both pipes 61, 64 and 81, 84 are also connected to each other through a variable leak valve 66, 86 which is kept closed during normal operation.

As the hydrogen detector according to this invention is constructed as described above, the internal wall surface area of the pipes in the static equilibrium measuring system can be minimized and A/d of the metal membrane in the static equilibrium measuring system can be larger independently of that of the dynamic equilibrium measuring system, to thereby improve the measuring accuracy, and hence calibration precision, in the static equilibrium operation. Also, in the calibration test, there are required no troublesome operations for changeover of the stop valve and alternate prosecution of the static and dynamic equilibrium operations. Thus, it is possible with the apparatus of this invention to perform the measuring operation with ease and at high precision with no need of making any manual operation for the detector itself.

What is claimed is:

1. A hydrogen detector of the type having a metal membrane partitioning the interior of the detector into a fluid section and a vacuum section, wherein two units of said metal membrane are provided and vacuum pipes are provided independently in connection to the respective units of said metal membrane, one of said vacuum pipes being connected to a vacuum gauge for static equilibrium measurement and the other vacuum pipe being connected to an ion pump or a set of an ion pump and a vacuum gauge both for dynamic equilibrium measurement, said metal membrane for static equilibrium measurement being greater in A/d, A being membrane surface area and d being membrane thickness, than said metal membrane for dynamic equilibrium measurement.

2. The hydrogen detector according to claim 1, wherein both of said vacuum pipes are connected to each other by a pipe provided with a stop valve.

3. The hydrogen detector according to claim 1, wherein said metal membranes are tubular in shape, closed at the protuberant end, and extend into the respective vacuum pipes, and a fluid inlet pipe is inserted into each of said tubular metal membranes in the fluid section.

4. The hydrogen detector according to claim 3, wherein said metal membranes are tubular in shape with both ends thereof opened, and the proximal end of the tubular metal membrane is secured to a support block provided on the interior of the vacuum pipe, and the protuberant end of the tubular metal membrane is closed by an end plate made of the same material as the support block.

5. The hydrogen detector according to claim 3, wherein the tubular metal membrane for dynamic equilibrium measurement comprises a short tubular metal membrane portion and a cylindrical tube portion connected to the end of the short tubular metal membrane portion, the protuberant end of the cylindrical tube portion being closed, the whole length of tubular metal membrane for dynamic equilibrium measurement being substantially equal to the length of the tubular metal membrane for static equilibrium measurement.

6. The hydrogen detector according to claim 3, wherein a plurality of tubular metal membranes into each of which the fluid inlet pipe is inserted are provided in parallel in the vacuum pipe for static equilibrium measurement.

* * * * *